(12) United States Patent
Glukhovsky et al.

(10) Patent No.: US 7,200,253 B2
(45) Date of Patent: Apr. 3, 2007

(54) MOTILITY ANALYSIS WITHIN A GASTROINTESTINAL TRACT

(75) Inventors: Arkady Glukhovsky, Santa Clarita, CA (US); Gavriel Meron, Petach Tikva (IL); Ofra Zinaty, Haifa (IL)

(73) Assignee: Given Imaging Ltd., Yoqneam (IL)

( * ) Notice: Subject to any disclaimer, the term of this patent is extended or adjusted under 35 U.S.C. 154(b) by 0 days.

(21) Appl. No.: 11/201,217

(22) Filed: Aug. 11, 2005

(65) Prior Publication Data

US 2005/0281446 A1 Dec. 22, 2005

Related U.S. Application Data

(63) Continuation of application No. 10/175,148, filed on Jun. 20, 2002, now Pat. No. 6,944,316, which is a continuation of application No. PCT/IL02/00386, filed on May 19, 2002.

(60) Provisional application No. 60/299,178, filed on Jun. 20, 2001.

(51) Int. Cl.
*G06K 9/00* (2006.01)
*A61B 1/04* (2006.01)

(52) U.S. Cl. .................. 382/128; 600/117; 600/160

(58) Field of Classification Search .............. 382/128; 348/65, 77; 128/922; 600/109, 117, 160
See application file for complete search history.

(56) References Cited

U.S. PATENT DOCUMENTS

| | | | |
|---|---|---|---|
| 4,278,077 A | 7/1981 | Mizumoto | 128/4 |
| 5,604,531 A | 2/1997 | Iddan et al. | 348/76 |
| 5,993,378 A | 11/1999 | Lemelson | 600/109 |
| 6,240,312 B1 | 5/2001 | Alfano et al. | 600/476 |
| 6,428,469 B1 | 8/2002 | Iddan et al. | 600/109 |
| 6,621,917 B1* | 9/2003 | Vilser | 382/128 |
| 6,709,387 B1 | 3/2004 | Glukhovsky et al. | 600/109 |
| 2002/0103417 A1 | 8/2002 | Gazdzinski | 600/109 |

OTHER PUBLICATIONS

Rowell, Nancy D., Endoscopes Go Wireless Biophotonics In Action Photonics Spectra Mar. 2001.
PCT Search Report International Application No.: PCT/IL02/00386 International Filing Date: May 19, 2002.

* cited by examiner

*Primary Examiner*—Andrew W. Johns
(74) *Attorney, Agent, or Firm*—Pearl Cohen Zedek Latzer, LLP (57) ABSTRACT

A system and method for measuring and analyzing motility within a body lumen such as the gastrointestinal (GI) tract, where an in vivo imaging device such as a capsule captures images and transmits the images to a processor, which calculates the motility of the device based on comparison of the images. Preferably, the processor compares the intensity of pairs of images or of elements of pairs of images, generates a variance for the compared images, and calculates the motility of the imaging device from the variances. The motility data may be presented to a user in various manners; for example, a plot of motility over time may be generated, or indications of low motility may be presented to the user of the system.

38 Claims, 4 Drawing Sheets

MOTILITY ANALYSIS WITHIN A GASTROINTESTINAL TRACT

PRIOR APPLICATION

The application is a Continuation Application of U.S. patent application Ser. No. 10/175,148, filed Jun. 20, 2002, now patent application Ser. No. 6,944,316, which is a continuation of International Patent Application No. PCT/1L02/00386, filed on May 19, 2002 which in turn claims the benefit of U.S. Provisional Application No. 60/299,178, filed on Jun. 20, 2001, all of which are incorporated by reference herein in their entirety.

FIELD OF THE INVENTION

The present invention relates to a method and system for analysis of motility within a body lumen, such as within the gastrointestinal (GI) tract.

BACKGROUND OF THE INVENTION

Normal peristalsis within a GI tract is responsible for transporting swallowed food and aiding in digestion and eventual evacuation. Peristalsis results in pressure waves moving along the GI tact, in turn resulting in the motility of a bolus within the GI tract. Thus, changes in motility along the GI tract may indicate normal conditions such as food passing from one section of the GI tract to another (such as passage from the stomach to the small intestine or passage from the small intestine to the large intestine). Certain pathological conditions can alter the normal motility within the GI tact. Low motility may be caused by an obstruction or blockage or by other pathological conditions. It is often difficult to detect areas of low or abnormal motility within the GI tract, since these areas may be in difficult to reach locations. It is difficult to "see" inside the tract, especially in sections that are hard to reach via conventional methods, such as the small intestines. Motility is the result of complex neuro-physiological processes. Motility disorders may be caused by nervous disorders and may not necessarily be visible as, for example, physiological changes in the intestinal tissue.

Various in vivo measurement systems for examining a body lumen are known in the art. A commonly known and used type of system is an endoscope. Endoscopes are devices which include a tube (either rigid or flexible) and an optical system, and which are introduced into the body to view the interior The range of endoscopes—the portion of the GI tract, which endoscopes are capable of viewing—is limited. Endoscopes are usually not helpful in providing information on GI tract motility. Probes, such as pressure probes, may be used to measure peristaltic pressure waves. Other systems that may be used for obtaining information on GI tract motility include dissolvable vehicles containing non dissolving markers that are visible by X-ray. The vehicle is ingested and the progression of the markers, which are released in the GI tract once the vehicle is dissolved, can be followed by X-ray. This method, however, can not be used for continuous monitoring and also exposes the patient to hazardous X-rays.

A non hazardous system and method for monitoring and/or analyzing movement along the entire GI tract is needed, inter alia, for facilitating the understanding of GI tract motility and for expanding diagnostic (and perhaps therapeutic) possibilities in the GI tract.

SUMMARY OF THE INVENTION

An exemplary embodiment of the system and method of the present invention measures and analyzes motility within a body lumen such as the GI tract. In another embodiment of the invention a method is provided for diagnosis of in vivo conditions in the GI tract of a patient. In one embodiment an in vivo imaging device such as an ingestible imaging capsule captures images and transmits the images to a processor, which calculates the motility of the device based on comparison of the images. In one embodiment the processor compares the intensity of pairs of images or of elements of pairs of images, generates an average difference for the compared images, and calculates the motility of the imaging device from the average differences. In other embodiments indicators, such as radio frequency (RF) signals, stain gauges, velocity meters or accelerometers may be used to calculate the motility of a device. In another embodiment a geometrical location or in vivo position of the device may be determined for later calculation of the motility. The motility data may be presented to a use in various manners; for example, a plot of motility over time may be generated, or indications of low or abnormal motility may be presented to the user of the system.

According to an embodiment of the invention motility analysis data is examined for at least one parameter, the parameter is compared to a reference and at least one condition in the GI tract is deduced from the comparison.

BRIEF DESCRIPTION OF THE DRAWINGS

The present invention will be understood and appreciated more fully from the following detailed description taken in conjunction with the drawings in which.

DETAILED DESCRIPTION OF THE INVENTION

In the following description, various aspects of the present invention will be described For purposes of explanation, specific configurations and details are set forth in order to provide a thorough understanding of the present invention. However, it will also be apparent to one skilled in the art that the present invention may be practiced without the specific details presented herein. Furthermore, well known features may be omitted or simplified in order not to obscure the present invention.

The present invention relates to a method and system for analyzing motility within a GI tract and for displaying motility to a user such as a health professional, who may use such data to, for example, diagnose pathologies. In an exemplary embodiment of the present invention, the motility of a capsule or other vehicle, which is propelled through the GI tract by the natural action of the GI tract is measured, giving an indication of the motility in the GI tract, in different portions of the GI tract. In one embodiment, the motility of the vehicle is calculated via an analysis of sequential images captured by the vehicle; the greater the difference between sequential images, the greater the motility.

Figure 1:
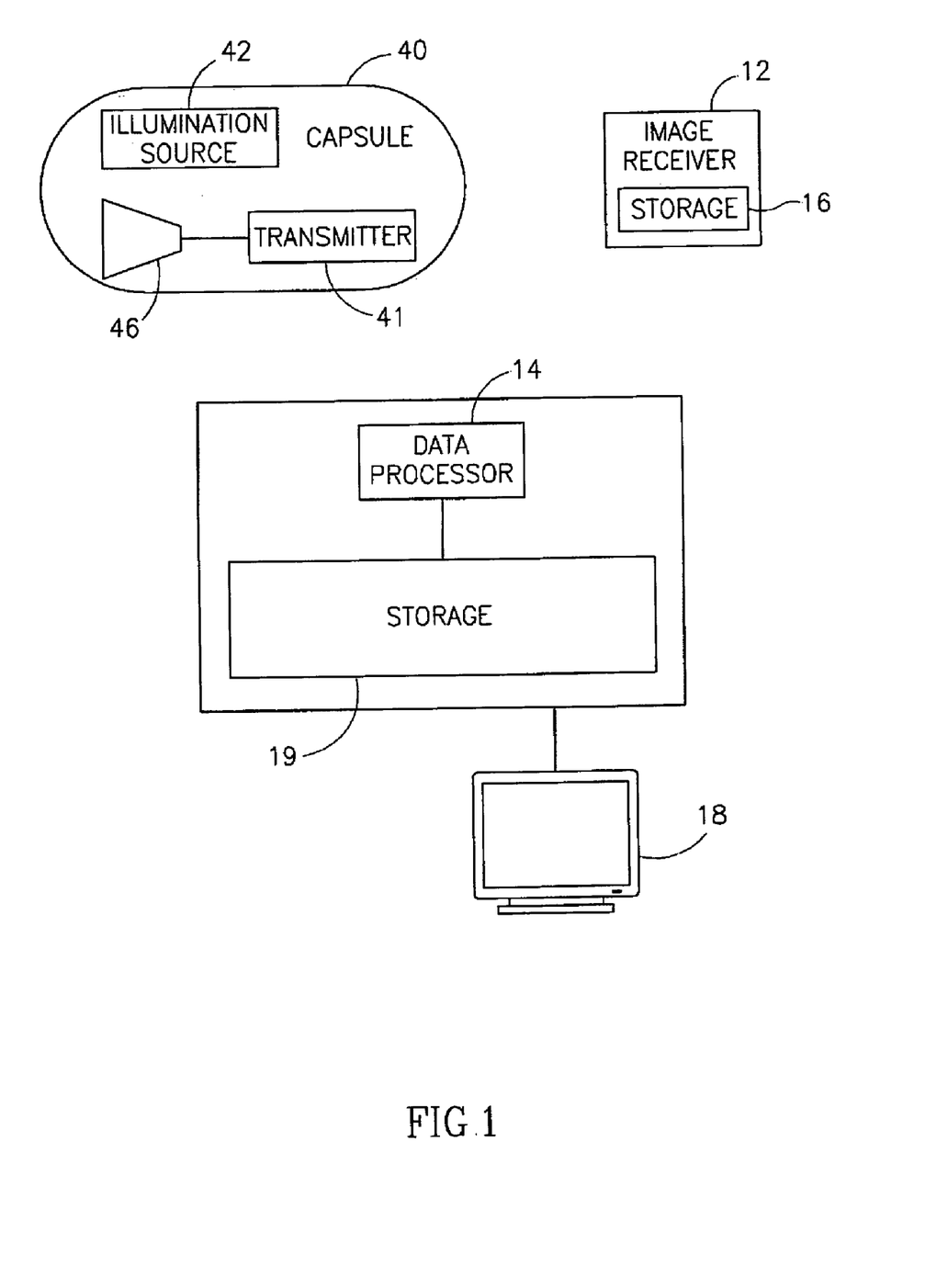
FIG. 1 is a schematic illustration of an in vivo imager system, according to one embodiment of the present invention.

Reference is made to FIG. 1, which shows a schematic diagram of an in vivo imaging system according to one embodiment of the present invention. In an exemplary embodiment, the system comprises a capsule 40 having an imager 46, for capturing images, an illumination source 42, for illuminating the body lumen, and a transmitter 41, for transmitting image and possibly other information to a receiving device. An optical system (not shown), including, for example, lenses or minors, may aid in focusing reflected light onto the imager 46. The capsule 40 is swallowed by a patient and preferably traverses the patient's GI tract. In alternate embodiments the capsule 40 may have different configurations and include other sets of components.

Preferably, while the capsule 40 traverses a patient's GI tract, the capsule 40 transmits image and possibly other data to components located outside the patient's body, which receive and process the data. Preferably, located outside the patient's body in one or more locations, are an image receiver 12, preferably including an antenna or antenna array, an image receiver storage unit 16, a data processor 14, a data processor storage unit 19, and an image monitor 18, for displaying, inter alia, the images recorded by the capsule 40 and motility information. In one embodiment, the image receiver 12 and image receiver storage unit 16 are small and portable, and are worn on the patient's body during recording of the images. Optionally, data processor 14, data processor storage unit 19 and monitor 18 may be part of a personal computer or workstation, which includes standard components such as processor 14, a memory, a disk drive, and input-output devices, although alternate configurations are possible.

Data processor 14 may include any standard data processor, such as a microprocessor, multiprocessor, accelerator board, or any other serial or parallel high performance data processor. Image monitor 18 may be a computer screen or a conventional video display, but may, in addition, be a prints or any other device capable of providing an indication of image and/or position data.

Preferably, the imager 46 is a suitable CMOS camera, such as a "camera on a chip" type CMOS manager specified by Given Imaging Ltd. of Israel and designed by Photobit Corporation of California, USA. In alternate embodiments, the imager 46 may be, for example, a CCD. The illumination source 42 may be, for example, a light emitting diode.

In operation, imager 46 captures images and sends data representing the images to transmitter 41, which transmits images to image receiver 12 using, for example, electromagnetic radio waves. Image receiver 12 transfers the image data to image receiver storage unit 16. After a certain period of time of data collection, the image data stored in storage unit 16 is sent to data processor 14 or data processor storage unit 19. For example, the image receiver storage unit 16 may be taken off the patient's body and connected to the personal computer or workstation which includes the data processor 14 and data processor storage unit 19 via a standard data link, e.g., a serial or parallel interface of known construction. The image data is then transferred from the image receiver storage unit 16 to the data processor storage unit 19. Data processor 14 analyzes the data and provides the analyzed data to the image monitor 18, where a health professional views, for example, the image data and motility information.

The image data collected and stored may be stored indefinitely, transferred to other locations, or manipulated or analyzed. A health professional may use the images to diagnose pathological conditions of the GI tract and, in addition, the system may provide information about the location of these pathologies. While, using a system where the data processor storage unit 19 first collects data and then transfers data to the data processor 14, the image data is not viewed in real time, other configurations allow for real time viewing. In such systems, image motility may be calculated and displayed in real time.

The image monitor 18 presents the image data, preferably in the form of still and moving pictures, and in addition may present other information. In an exemplary embodiment, such additional information may include, but is not limited to, absolute time elapsed for the current image being shown and the relative or absolute motility of the capsule 40, over the course of the capsule's travel through the GI tract, and/or at the time corresponding to the current image being displayed. Absolute time elapsed for the current image being shown may be, for example, the amount of time that elapsed between the moment the capsule 40 was first activated and the image receiver 12 started receiving transmissions from the capsule 40, and the moment that the current image being displayed was captured. Various methods may be used to display the motility of the capsule 40; such methods are discussed below. In an exemplary embodiment, the various categories of information are displayed in windows. Multiple monitors may be used to display image and other data.

Preferably, the image data recorded and transmitted by the capsule 40 is digital color image data, although in alternate embodiments other image formats may be used. In an exemplary embodiment, each frame of image data includes 256 rows of 256 pixels each, each pixel including data for color and brightness, according to known methods For example, in each pixel color may be represented by a mosaic of four sub-pixels, each sub-pixel corresponding to primaries such as red, green, or blue (where one primary is presented twice). The brightness of the overall pixel is recorded by a one byte (ie, 0–255) brightness value. Preferably, images are stored sequentially in data process storage unit 19. The stored data is comprised of one or more pixel properties, including color and brightness.

While, preferably, information gathering, storage and processing is performed by certain units, the system and method of the present invention may be practiced with alternate configurations. For example, components providing for motility analysis may be located inside a capsule or, alternately, on a portable device worn on the patient. Furthermore, the components gathering image information need not be contained in a capsule, but may be contained in any other vehicle suitable for traversing a lumen in a human body, such as an endoscope, stent, catheter, needle, etc.

The in vivo imager system may collect a large volume of data, as the capsule 40 may take several hours to traverse the GI tract and may record images at a rate of, for example, two images every second, resulting in the recordation of tens of thousands of images. The series of still images collected may later be presented as still images or as a moving image of the traverse of the GI tract. The image recordation rate (or frame capture rate) may be varied; for example, the image recordation rate may be varied based on capsule motility. While in the GI tact, the capsule 40 undergoes intermittent motion with long residence time at some positions. These periods of long residence may be normal or can be due to pathologies, such as blockages, within the digestive tract. The system and method of the present invention aids health professionals in monitoring the capsule motion and in diagnosing and locating, for example, areas of blockage. In addition, changes in motility may be indicative of a normal condition such as the passage of the capsule 40 from one section of the GI tract to another, and thus the system and method of the present invention may use motility data to determine the position of the capsule 40 or other diagnostic device.

In an exemplary embodiment, each image $P_i$ in the data stream of images is compared to its predecessor image $P_{i-1}$ (or to other previous image $P_{i-n}$) to determine the motility of the capsule 40 during the time between the capture of the two images. Various methods of determining motility based on image comparison may be used. In an exemplary embodiment, the system and method analyze image similarity to obtain a measure of motility. It can be assumed that the more similar two compared images are, the slower the movement of the capsule 40 between the times the two images are captured. In an extreme situation—if the two compared images are identical—it can be assumed the capsule 40 has not moved between the times the two images were captured. If two compared images differ greatly, it is an indication that the capsule 40 was moving quickly between the times of capture of the images. This concept is illustrated further in FIGS. 2A and 2B.

Figure 2A:
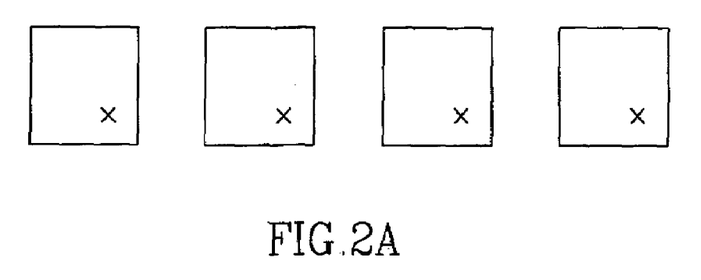
FIGS. 2A and 2B show a simplified series of images, which may be captured by the vivo imager system of FIG. 1.
Figure 2B:
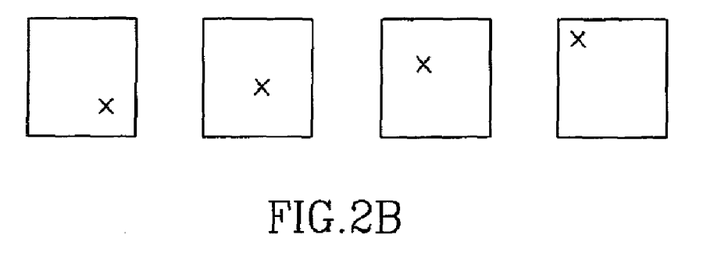

FIGS. 2A and 2B show a simplified series of images, which may be captured by the vivo image system of FIG. 1. Referring to FIGS. 2A and 2B, a comparison of images provides information about the speed of the capsule 40. In FIG. 2A, several consecutive images are shown in which a specific point X is located in approximately the same location within each of the images. In FIG. 2B, the same point X is located in varying positions within the images, taken over the same period of time. It can be inferred that the images shown in FIG. 2A were taken by an imager whose position did not change by much between the times each image was taken, and thus which had relatively low motility. It can be inferred that the images shown in FIG. 2B were taken by an imager which is moving more rapidly.

Preferably, data processor storage unit 19 stores a series of images recorded by a capsule 40. The images may be combined consecutively to form a moving image of the images the capsule 40 recorded as it moved through a patient's GI tract. This moving image may be displayed in a window on monitor 18. The moving image may be frozen to view one frame, speeded up, or reversed; sections may be skipped; or any other method for viewing an image may be applied to the moving image. While the following discussion relates to the case where data from a capsule 40 is stored for later use, the system and method of the present invention may be used with systems allowing for real time viewing of image data.

In an exemplary embodiment, to determine the motility of the capsule 40 at various points during its journey through the GI tract, data processor 14 first receives image data from data processor storage unit 19. Data processor 14 then compares each image $P_i$ in the data stream to its predecessor image $P_{i-1}$ (or $P_{i-n}$) to determine the motility of the capsule 40 during the time between the capture of the two images.

The comparison of images may be made on a pixel-by-pixel basis or, alternatively, on a pixel cluster basis. In alternate embodiments, images may be compared without division into sections such as pixels or clusters. In an exemplary embodiment, the 256×256 pixel grid of each image is divided into a 32×32 grid of pixel clusters, to form 1,032 clusters. In alternate embodiments, other methods of dividing an image may be used. Based on the comparison of the two images, data processor 14 calculates the relative motility for the capsule 40 that captured the images for the time period between the capture of the two images. In an exemplary embodiment, the resulting motility value at a certain point is a relative number on a certain scale, which indicates the motility of the capsule 40 relative to other points in the capsule's traverse of the GI tract. In alternate embodiments, absolute motility may be calculated.

The motility calculation is repeated for all or a set of images in the series of images, and a series of motility values is generated. The resulting motility values may be presented to the user in various manners. Preferably, the monitor 18 includes a window displaying an image frame or a moving image, a window showing the absolute time elapsed in the image series for the frame being displayed (or the current point in the moving image), and a window including a chart of the relative motility of the capsule 40 plotted against time. An indication may be provided on the display on monitor 18 connecting certain motility values, or regions having low motility or certain motility patterns, to images or sections of the moving image. The user may be able to indicate certain motility values or a portion of the motility chart or plot by, for example, clicking with a mouse, and have displayed the corresponding still or moving image.

Additional windows may display other data. For example, the position of the capsule 40 as it traverses the GI tract may be graphed as a two-dimensional rendering of the three-dimensional path; such data may be combined with or linked to image or motility data. Areas of low motility, or areas of altered or abnormal patterns of motility, may be indicated on such a capsule path representation by using, for example, color changes or labels.

In one embodiment, a spectral analysis of the motility data may be performed, and the spectral analysis may be presented to the user or may be used for diagnostic or other purposes. In a normal human GI tract, peristaltic waves are typically generated with some repetition. A spectral analysis, according to known methods, of the peristaltic waves of different time periods or sections of the series of motility data, may be performed and, for example, presented to the user. Such a spectral analysis may present, for example, the frequency of repetition of peristaltic waves at different times or positions in a vehicle's travel through the GI tract. In alternate embodiments, other visual indications of motility may be provided According to one embodiment of the invention, motility data can be examined for at least one parameter or measurement that may be presented as, for example, a specific pattern or representation of a pattern in a spectral analysis of the motility data or a specific repetition or representation of a repetition of peristaltic waves. The parameter, possibly represented by a pattern or specific patterns, can be compared to a reference, such as a parameter value in a normal or healthy individual or a specific pattern typical of a pathological condition in the GI tract. The comparison results can indicate, for example, a prevailing condition (or conditions) in the GI tract, thereby providing a diagnostic tool for identifying conditions in the GI tract. For example, a spectral analysis may be performed on the motility of an in-vivo device. The spectral analysis may be represented, for example, as a graph of movement waves over time; other ways of representing a spectral analysis may be used. A pattern matching module (for example, processor 14 operating according to software) may seek to match the recorded spectral analysis to spectral analyses corresponding to various conditions, and a match or near match may be reported to a user.

Figure 3:
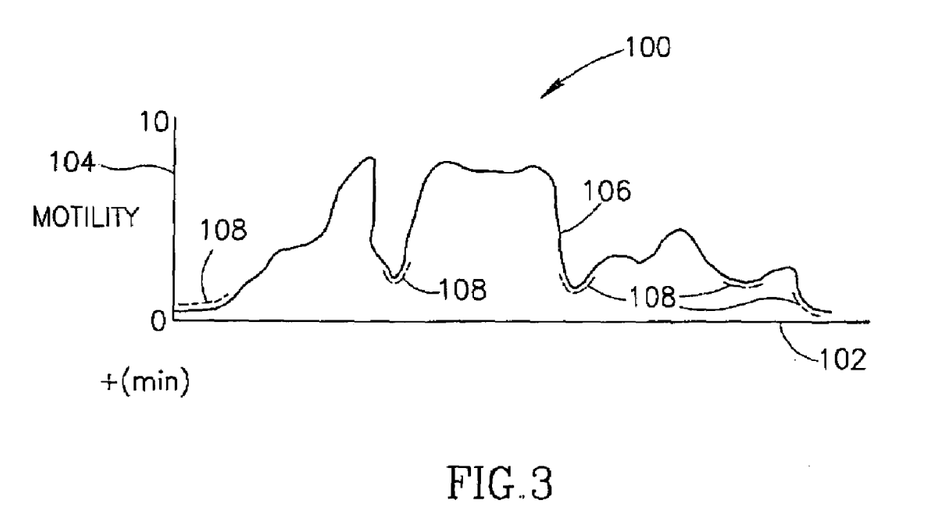
FIG. 3 depicts a motility chart produced by the system of FIG. 1, according to one embodiment of the present invention.

FIG. 3 depicts a motility chart produced, for example, by the system of FIG. 1, according to one embodiment of the present invasion. The plot or chart 100 includes a time axis 102, a relative motility axis 104, and a motility plot or graphing 106. Preferably, if the health professional indicates a certain point along the motility chart, using, for example, a pointing device such as a mouse, the corresponding image appears in the image window. While, in an exemplary embodiment the relative motility is expressed in arbitrary units (for example, 0 to 10, adjusted logarithmically), other methods of expressing motility may be used, and absolute motility may also be expressed.

The chart 100 may include indications of low motility 108, which may be, for example, marks or colored or shaded regions indicating areas where motility is low enough to warrant investigation by a professional. The data processor 14 may filter for certain patterns of motility, where such patterns may commonly indicate either normal conditions, such as passage between areas of the GI tract, or pathological conditions. Such conditions may be labeled on the motility chart. In response to such indications of low motility, the health professional may click or otherwise indicate the area on the motility chart in question, and view images (still or moving) of the corresponding area in the GI tract.

Any number of methods may be used to analyze the image data to form motility data For example, motility analysis may be based on a calculation of the difference in a given property between corresponding pixels of two, not necessarily consecutive frames; a calculation of the cross-correlation function between two, not necessarily consecutive, frames, a calculation of the changes of local statistical distributions in two, not necessarily consecutive, frames; or a calculation of the changes between corresponding local statistical distributions in two, not necessity consecutive, frames. Local statistical distributions may include, but are not limited to, the mean, the variance, or the standard deviation of pixel clusters.

In an exemplary embodiment, each image in a pair of images being compared is divided into a number of sections. Each section in the first image is compared to the corresponding section in the second image. The variance of the difference of the brightness for the two sections, normalized by the number of sections, is calculated. The variance is used to ascertain the relative motility of the vehicle capturing images, which in an exemplary embodiment is capsule 40.

Figure 4:
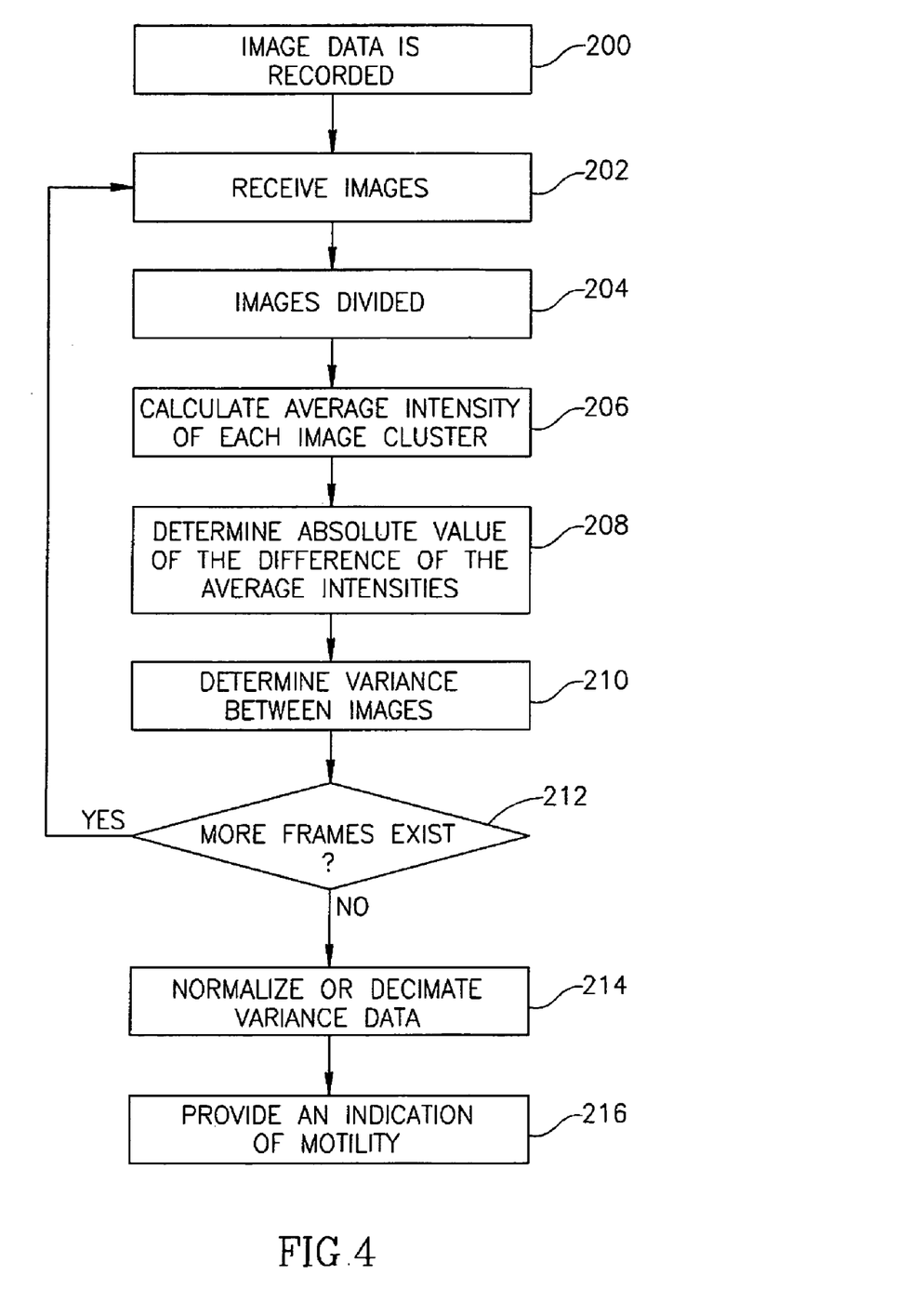
FIG. 4 is a flow chart showing the steps for determining the motility of a device recording images from a body lumen according to an exemplary embodiment of the present invention.

Reference is now made to FIG. 4, a flow chart showing the steps for determining the motility of a device recording images from a body lumen according to an exemplary embodiment of the present invention.

In step 200, image data is recorded by the capsule 40 and transmitted to the data processor storage unit 19. In step 202, data processor 14 receives from data processor storage unit 19 images $P_i$ and $P_{i+x}$, where x is usually, but not necessarily, 1. If the stream of images is too lengthy or rapid, a decimation may be performed and non-adjacent images may be compared, e.g., image $P_i$ and $P_{i+x}$, where x>1.

In step 204, data processor 14 may divide each of the two images into pixel clusters, sections or cells. In an exemplary embodiment, each image $P_i$ is divided into 1024 clusters $A_i(m,n)$, where 1<m<32 and 1<n<32.

In step 206, data processor 14 calculates the average intensity $I_{Ai(m,n)}$ of each cluster $A_i(m,n)$ of each of image $P_i$ and $P_{i+x}$. Preferably, the intensity value for a cluster is the average of the brightness values for the pixels in the cluster.

A matrix of the intensities of the clusters may be formed for each image. Alternate methods of calculating intensity may be used; for example, color data may be used to compare images.

In step 208, data processor 14 determines the absolute value $D_i(m,n)$ of the difference of the average intensities I of $A_i(m,n)$ and $A_{i+x}(m,n)$ of corresponding clusters A(m,n) in the frames $P_i$ and $P_{i+x}$. $D_i(m,n)$ is defined as:

$$D_i(k,l)=|I_{A_i(k,l)}-I_{A_{i+x}(k,l)}|$$

A matrix of the absolute values of differences is formed, one value being generated for each cluster compared.

In step 210, data processor 14 determines the average difference (Diff) between the two images. In an exemplary embodiment, the average difference is calculated by first subtracting from each absolute value in the matrix created in step 208 the average value of all the differences in the matrix, summing the resulting values, taking the square root of the resulting sum, and dividing by the number of the differences in the matrix (in an exemplary embodiment 1024). This may be expressed by the formula:

$$Diff = \sum_{m=1,32; n=1,32} D_i(m,n)/1024$$

where Diff corresponds to the average of the values in the difference matrix.

In an exemplary embodiment the resulting average difference is a value from 0 to U, where U is an arbitrary upper limit which depends upon the parameters. A low average difference indicates that the measured value (in an exemplary embodiment, brightness) varies little be the compared frames, and a high value of the average difference indicates that the measured value varies a large amount. A low difference is an indication of low motility, as, if the capsule 40 is not moving quickly, the images in the two compared frames will not vary by a large amount.

In step 212, if more frames exist in the image stream, data processor 14 returns to step 202. If no more flames exist data processor 14 proceeds to step 214. At this point, the difference data exists as a series of difference values, one for each frame pair analyzed, preferably X-1 variances, where X is the number of frames analyzed.

In step 214, data processor 14 may normalize or decimate the resulting difference data to an arbitrary scale. This normalized data represents the relative motility of the capsule 40. In an exemplary embodiment, each difference datum, represented as a value from 0–U, is normalized to a number between 0 and 10; other ranges may be used. The normalization process may be linear or may be non-linear—for example, a logarithmic function may be used. In alternate embodiments, other normalization or decimation functions may be used, for example, the difference data may be translated to a set of integers. During normalization, various functions, such as logarithmic functions, may be applied to the data.

In step 216, data processor 14 provides an indication of motility for the capsule 40. In an exemplary embodiment, data processor 14 creates a plot or graph of relative motility over time for display on the monitor 18 using the normalized values created in step 214. Data processor 14 may augment the graph with indications of low motility or indications of certain conditions. For example, sections of the graph where motility falls below a certain threshold may be marked in a certain color or pattern, or may be otherwise labeled.

Figure 5A:
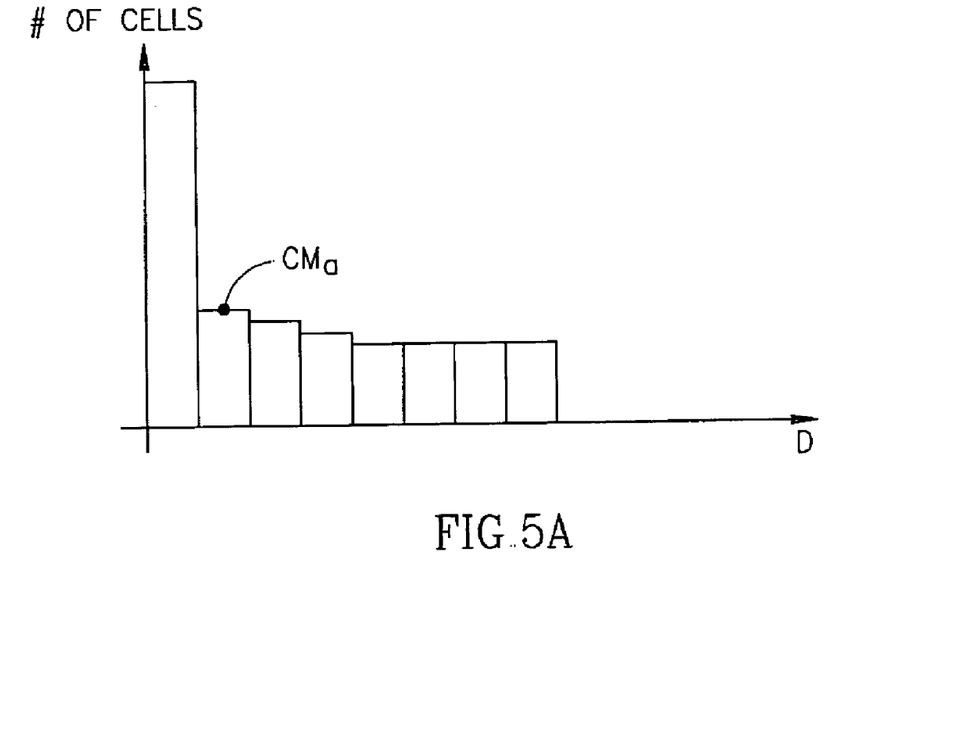
FIGS. 5A and 5B are histograms used to calculate motility according to an embodiment of the present invention.
Figure 5B:
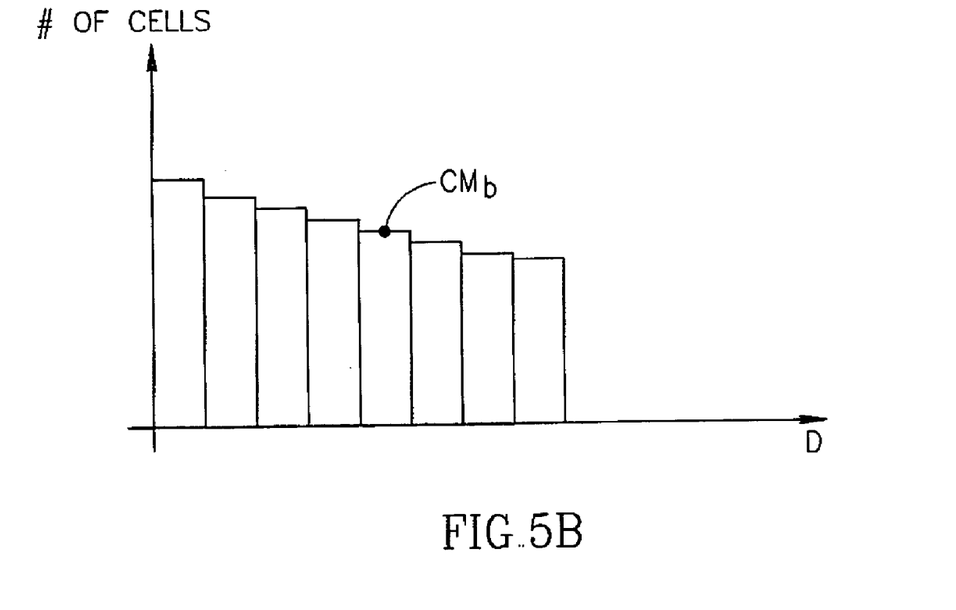

In alternate embodiments, other methods of analyzing the image data to form motility data may be used. For example, for each frame pair, data processor 14 may organize the difference values $D_i(k,l)$ into a chart, for example, a histogram, as shown in FIGS. 5A and B. FIGS. 5A and B depict histograms used to calculate motility according to an embodiment of the present invention. Referring to FIGS. 5A and B, the absolute value $D_i(m,n)$ of the difference is plotted on the x-axis of the histograms and the number of corresponding pairs of cells, $A_i(m,n)$ and $A_{i+x}(m,n)$, which have a difference of magnitude $D_i(k,l)$, is plotted on the y-axis. The histogram of in FIG. 5A presents a histogram of cells in relatively similar frames, while the histogram of FIG. 5B shows a histogram of cells in significantly different frames. It should be readily apparent that if two images are similar, the histogram of the differences in the cells of those images are concentrated at low values of $D_i(m,n)$. It should also be readily apparent that the center of mass $CM_a$ (the average difference between the two images) of the histogram shown in FIG. 5A has a smaller value of D than the center of mass $CM_b$ of the histogram shown in FIG. 5B, and corresponds to a slower moving capsule 40. To calculate the difference between the two frames, processor 14 determines the centers of mass CM of the histograms corresponding to the two frames, and creates a difference value based on the location of the CM. In another embodiment image analysis may be used to determine the location of the capsule 40 in vivo (for example by identifying image parameters that are typical to a specific region in the GI tract) and the position information together with known factors; either the time that has elapsed during the translocation of the capsule 40 or the velocity of the capsule 40 along its path, can be used to calculate the motility. Similarly, the location of the capsule may be determined by other known methods and the location information can be used to calculate motility.

In alternate embodiments, methods of measuring motility may be used which are not based on image analysis. Fat example, the capsule 40 may include an accelerometer which determines the instantaneous acceleration of capsule 40 as it moves through the GI tract. An integrator may convert the acceleration data to velocity data, and this velocity data may be used by the data processor to determine motility. Alternately, a pressure sensor or shear gauge attached to the capsule 40 may detect peristaltic induced pressure or movement exerted by the walls of the small intestine. The relationship between pressure and velocity may be determined empirically, and then utilized to determine the velocity or relative velocity of the capsule 40. A sensor in the capsule 40 may detect movement relative to an artificially induced magnetic field, which is generated in the area of the patient's GI tract. The magnetic field induces a current in a coil in the sensor, whose magnitude is a function of the velocity of the coil through the field. Data on the induced current is converted to motility information. Further, external sensors may also be used, such as a Doppler, ultrasound unit, which continuously tracks the capsule 40. Additionally, the receiver 12, which, according to one embodiment is adapted to receive RF signals from the transmitter 41, may be used to monitor the intensity of the transmitted signal, whereas signals of unchanging intensities indicate that the transmitter 41 (and hence the capsule 40) is unmoving and signals of different intensities indicate that the transmitter 41 is moving. One or more of the above methods, or other methods, may be combined to provide a determination of capsule motility.

It will be appreciated by persons skilled in the art that the present invention is not limited by what has been particularly shown and described hereinabove. Rather the scope of the invention is defined by the claims that follow:

The invention claimed is:

1. A system for displaying in-vivo image data of a body lumen comprising:
   an in-vivo imaging device configured for moving within a body lumen;
   a receiver to receive image frames captured by said in-vivo device; and
   a display comprising:
   a first window displaying a moving image wherein the moving image includes a series of image frames captured by said in-vivo device; and
   a second window displaying information against time, wherein the information corresponds to the image frames being displayed in said first window.

2. The system according to claim 1 wherein the information comprises motility information of said in-vivo device in said lumen.

3. The system according to claim 1 comprising a label on said information.

4. The system according to claim 3 wherein the label is marked by color.

5. The system according to claim 3 wherein clicking on the label enables viewing of a corresponding image frame of said moving image.

6. The system according to claim 3 wherein said label indicates a frame with low motility of the in-vivo device.

7. The system according to claim 1, wherein said display is configured to display a position of the in-vivo device in said body lumen.

8. The system according to claim 7 wherein said display of said position of said device comprises a rendering of a path of said device.

9. The system according to claim 7 wherein said display of position in said body lumen is linked to an image frame in said series captured by said device at said position in said body lumen.

10. The system according to claim 7 wherein said display of position in said body lumen is linked to said information displayed in said second window.

11. The system according to claim 7 wherein said display of position comprises an indication of an area corresponding to an altered pattern of said information.

12. The display according to claim 11 wherein the indication comprises a color change.

13. The display according to claim 1 wherein said images and said information are displayed in real time.

14. A method of displaying data obtained from an in-vivo imaging device configured for moving within a body lumen comprising:
    capturing images of a body lumen with an in-vivo imaging device;
    displaying a moving image wherein the moving image includes a series of said images;
    displaying information against time, wherein the information corresponds to the images being displayed.

15. The method according to claim 14 wherein the information comprises motility of said in-vivo device in said body lumen.

16. The method according to claim 14 wherein the displaying a moving Image and the displaying information is in real time.

17. The method according to claim 14 comprising labeling a section of the information.

18. The method according to claim 17 wherein the labeling is by user indication.

19. The method according to claim 14 comprising displaying a position of the in-vivo device in said body lumen.

20. The method according to claim 19 comprising linking said display of said position to said images of said moving image.

21. The method according to claim 19 comprising linking an area of said display of position to an area of said display of information.

22. The method according to claim 19 comprising indicating on said display of position an area corresponding to an altered pattern of said display of information.

23. The method according to claim 22 wherein the indicating is by color change.

24. A method far displaying in vivo data, the method comprising:
storing images received from an in vivo imaging system;
analyzing pixel properties of the stored images;
displaying an image frame on a monitor;
displaying on the monitor an indication of information based on analysis of pixel properties of the image frame being displayed; and
clicking on the indication of information being displayed to display an image frame corresponding to the indication.

25. The method according to claim 24 wherein the analyzing pixel properties of the stored images comprises analyzing sequential images received from the in vivo device.

26. The method according to claim 24 wherein pixel properties is selected from a group including: brightness, intensity, and color data.

27. The method according to claim 24 wherein the indication is a color indication.

28. The method according to claim 24 comprising displaying a time elapsed far the image frame being displayed.

29. The method according to claim 24 comprising displaying a series of the images in a moving image.

30. The method according to claim 24 comprising displaying a plot, the plot comprising a time axis and an indication mark.

31. The method according to claim 30 wherein the indication mark includes color.

32. The method according to claim 30 wherein the plot comprises an in vivo location indication.

33. A method for displaying in vivo data, the method comprising:
storing images received from an in vivo imaging system;
analyzing pixel properties of the stored images;
displaying an image frame on a monitor;
displaying on the monitor an indication of information based on analysis of pixel properties of the image frame being displayed; and
displaying on the monitor an indication of motility information based on the analysis of pixel properties of the stored images.

34. A system for displaying in vivo data, the system comprising an in vivo imaging capsule for obtaining and transmitting image data to an external receiver;
a receiver for receiving image data from the capsule, said receiver connected to a monitor;
a monitor to display an image frame, a time axis and a color indication, the color indication corresponding to pixel data analysis of the image data.

35. The system according to claim 34 comprising a pointing device far clicking to display an image frame corresponding to the color indication.

36. The system according to claim 34 comprising a pointing device for clicking to display an image frame corresponding to the time axis.

37. The system according to claim 34 wherein the image data is of sequential images.

38. The system according to claim 34 wherein the color indication is to indicate motility of the capsule within the gastrointestinal tract.

* * * * *

UNITED STATES PATENT AND TRADEMARK OFFICE
CERTIFICATE OF CORRECTION

| | | |
|---|---|---|
| PATENT NO. | : 7,200,253 B2 | Page 1 of 1 |
| APPLICATION NO. | : 11/201217 | |
| DATED | : April 3, 2007 | |
| INVENTOR(S) | : Arkady Glukhovsky et al. | |

It is certified that error appears in the above-identified patent and that said Letters Patent is hereby corrected as shown below:

In the Claims

Col. 11, line 15 please amend claim 24 to read as follows:

24. (Currently Amended) A method [far] <u>for</u> displaying in vivo data, the method comprising:

storing images received from an in vivo imaging system;

analyzing pixel properties of the stored images;

displaying an image frame on a monitor;

displaying on the monitor an indication of information based on analysis of pixel properties of the image frame being displayed; and clicking on the indication of information being displayed to display an image frame corresponding to the indication.

Col. 11, line 36 please amend claim 28 to read as follows:

28. (Currently Amended) The method according to claim 24 comprising displaying a time elapsed [far] <u>for</u> the image frame being displayed.

Signed and Sealed this
Fifteenth Day of September, 2015

Michelle K. Lee
*Director of the United States Patent and Trademark Office*

(12) EX PARTE REEXAMINATION CERTIFICATE (10205th)
United States Patent
Glukhovsky et al.

(10) Number: US 7,200,253 C1
(45) Certificate Issued: Jun. 26, 2014

(54) MOTILITY ANALYSIS WITHIN A GASTROINTESTINAL TRACT

(75) Inventors: Arkady Glukhovsky, Santa Clarita, CA (US); Gavriel Meron, Petach Tikva (IL); Ofra Zinaty, Haifa (IL)

(73) Assignee: Given Imaging Ltd., Industrial Park, Yoqneam Ilite (IL)

Reexamination Request:
No. 90/012,505, Dec. 19, 2012

Reexamination Certificate for:
Patent No.: 7,200,253
Issued: Apr. 3, 2007
Appl. No.: 11/201,217
Filed: Aug. 11, 2005

Related U.S. Application Data (63) Continuation of application No. 10/175,148, filed on Jun. 20, 2002, now Pat. No. 6,944,316, which is a continuation of application No. PCT/IL02/00386, filed on May 19, 2002.

(60) Provisional application No. 60/299,178, filed on Jun. 20, 2001.

(51) Int. Cl.
*G06K 9/00* (2006.01)
*A61B 1/04* (2006.01)
*A61B 1/06* (2006.01)

(52) U.S. Cl.
USPC .................................... 382/128; 601/160

(58) Field of Classification Search
None
See application file for complete search history.

(56) References Cited

To view the complete listing of prior art documents cited during the proceeding for Reexamination Control Number 90/012,505, please refer to the USPTO's public Patent Application Information Retrieval (PAIR) system under the Display References tab.

*Primary Examiner* — Robert Nasser (57) ABSTRACT

A system and method for measuring and analyzing motility within a body lumen such as the gastrointestinal (GI) tract, where an in vivo imaging device such as a capsule captures images and transmits the images to a processor, which calculates the motility of the device based on comparison of the images. Preferably, the processor compares the intensity of pairs of images or of elements of pairs of images, generates a variance for the compared images, and calculates the motility of the imaging device from the variances. The motility data may be presented to a user in various manners; for example, a plot of motility over time may be generated, or indications of low motility may be presented to the user of the system.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 14, 16, 34 and 35 are determined to be patentable as amended.

Claims 2-13, 15, 17-23 and 36-38, dependent on an amended claim, are determined to be patentable.

Claims 24-33 were not reexamined.

1. A system for displaying in-vivo image data of a body lumen comprising:
  an in-vivo imaging device configured for moving within a body lumen;
  a receiver to receive image frames captured by said in-vivo device; and
  *a processor programmed to process the image frames received by the receiver and to produce* a display comprising:
  a first window displaying a moving image wherein the moving image includes a series of image frames captured by said in-vivo device; and
  a second window displaying information against time, wherein the information corresponds to the image frames being displayed in said first window *and is based on analysis of pixel properties of the image frames*.

14. A method of displaying data obtained from an in-vivo imaging device configured for moving within a body lumen comprising:
  capturing images of a body lumen with an in-vivo imaging device;
  displaying a moving image wherein the moving image includes a series of said images; *and*
  displaying information against time, wherein the information corresponds to the images being displayed *and is based on analysis of pixel properties of the images*.

16. The method according to claim 14 wherein the displaying a moving [Image] *image* and the displaying information is in real time.

34. A system for displaying in vivo data, the system comprising*:*
  an in vivo imaging capsule for obtaining and transmitting image data to an external receiver;
  a receiver for receiving image data from the capsule, said receiver connected to a monitor;
  *a processor programmed to process the image data received by the receiver and to cause* a monitor to display*:* an image frame[,]*;* *and a chart comprising* a time axis and a color indication *displayed along the time axis*, the color indication corresponding to pixel data analysis of the image data.

35. The system according to claim 34 comprising a pointing device [far] *for* clicking to display an image frame corresponding to the color indication.

* * * * *